United States Patent [19]
LaPack et al.

[11] Patent Number: 5,233,876
[45] Date of Patent: Aug. 10, 1993

[54] APPARATUS AND METHODS FOR ON-LINE ANALYSIS OF ONE OR MORE PROCESS STREAMS

[75] Inventors: Mark A. LaPack; James C. Tou; Joanna L. Shih; William E. Martin, all of Midland, Mich.; Renne Y. Keith, Cincinnati, Ohio; Terry J. Nestrick, Midland, Mich.

[73] Assignee: The Dow Chemical Company, Midland, Mich.

[21] Appl. No.: 680,463

[22] Filed: Apr. 4, 1991

[51] Int. Cl.$^5$ .............................................. G01N 1/18
[52] U.S. Cl. .................... 73/863.23; 73/31.07; 73/14.56; 73/863,03; 73/863.33
[58] Field of Search .......... 73/863.12, 863.01, 863.02, 73/863.03, 863.21–863.25, 863.31, 863.32, 863.33, 31.07, 19.12, 61 R, 61 LM, 61.1 C, 61.1 R, 61.3, 863.61, 64.56; 210/96.1, 96.2

[56] References Cited

U.S. PATENT DOCUMENTS

| | | | |
|---|---|---|---|
| 3,190,725 | 6/1965 | Van Den Berg | 23/259.1 |
| 3,342,727 | 9/1967 | Bringle | 210/15 |
| 3,393,149 | 7/1968 | Conley et al. | 210/42 |
| 3,394,080 | 7/1968 | Hoffmann et al. | 210/59 |
| 3,596,767 | 8/1971 | Antonie | 210/96 |
| 3,615,235 | 10/1971 | Hrdina et al. | 73/61.1 R X |
| 3,624,710 | 11/1971 | Carter et al. | 73/61.1 R |
| 3,847,802 | 11/1974 | Lemke | 210/7 |
| 3,897,211 | 7/1975 | Ririe, Jr. | 73/23.35 X |
| 4,099,871 | 7/1978 | Sunshara et al. | 356/73 |
| 4,130,481 | 12/1978 | Chase et al. | 210/6 |
| 4,159,248 | 6/1979 | Taylor et al. | 210/96.1 |
| 4,160,734 | 7/1979 | Taylor et al. | 210/96.1 |
| 4,186,607 | 2/1980 | Porter et al. | 73/61.1 C |
| 4,280,910 | 7/1981 | Baumann | 210/614 |
| 4,341,633 | 7/1982 | Walder | 210/614 |
| 4,383,920 | 5/1983 | Muller et al. | 210/87 |
| 4,437,992 | 3/1984 | Saito et al. | 210/603 |
| 4,442,720 | 4/1984 | Apley et al. | 73/863.31 |
| 4,504,393 | 3/1985 | Davies | 210/614 |
| 4,510,243 | 4/1985 | Haga et al. | 435/167 |
| 4,516,580 | 5/1985 | Polanyi | 73/863.23 X |
| 4,581,143 | 4/1986 | Pepper, III | 210/614 |
| 4,690,755 | 9/1987 | Friedman et al. | 210/96.1 |
| 4,698,158 | 10/1987 | Fujii et al. | 210/610 |
| 4,727,758 | 3/1988 | Murdock | 73/863.24 X |
| 4,731,185 | 3/1988 | Chen et al. | 210/605 |
| 4,763,339 | 8/1988 | Jones | 73/863.23 X |
| 4,764,271 | 8/1988 | Acosta | 210/86 |
| 4,783,750 | 11/1988 | Smith | 364/497 |
| 4,816,158 | 3/1989 | Shimura et al. | 210/610 |
| 4,855,061 | 8/1989 | Martin | 210/709 |
| 4,898,672 | 2/1990 | Clifft et al. | 210/614 |
| 5,019,139 | 5/1991 | La Pack et al. | 55/158 |
| 5,090,257 | 2/1992 | Bruce | 73/863.03 |
| 5,093,269 | 3/1992 | Lenchartz et al. | 73/863.12 X |

FOREIGN PATENT DOCUMENTS 77258 4/1983 European Pat. Off. ......... 73/863.23
194031 11/1982 Japan.

Primary Examiner—Tom Noland
Attorney, Agent, or Firm—John K. McCulloch

[57] ABSTRACT

Apparatus and methods for on-line analysis of multiple stream processes wherein each stream has an influent delivered to a treatment zone and an effluent discharged from such zone and wherein both the influent and effluent are analyzed and the analyses compared for the evaluation of the effectiveness of the treatment.

58 Claims, 7 Drawing Sheets

APPARATUS AND METHODS FOR ON-LINE ANALYSIS OF ONE OR MORE PROCESS STREAMS

This invention relates to apparatus and methods for the continuous on-line analysis of one or more gas, liquid, or both gas and liquid, process streams for characterizing such streams and/or evaluating the efficiency of a chemical process that adds or removes substances to or from such streams

BACKGROUND OF THE INVENTION

The efficiency of chemical processes is becoming an increasingly important issue with the growing requirements of waste reduction and minimization of emissions of volatile compounds in air and water streams. Analytical on-line analysis of such streams can play a vital role in achieving and maintaining optimum process operating conditions.

As opposed to off-line analysis, on-line analysis can provide more efficient use of information about a process in terms of the amount of data, the quality of data, and the ability to respond to changes in the process as indicated by the data. For example, obtaining continuous temperature measurements by means of a thermocouple can provide a more statistically useful data set and more precise indications of changes in the process temperature than ca be obtained from intermittent manual measurements using a thermometer. The same is true for other traditionally measured process parameters such as pressure and pH, as well as the more sophisticated measurements of the composition of a chemical process.

Currently, on-line process composition analyses often are obtained from chromatographic, spectroscopic, or solid state chemical sensor techniques, as dictated by the nature of the analyte(s) and the process matrix. Although the speed, sensitivity, and selectivity of mass spectrometry make the technique attractive, on-line analysis by mass spectrometry has until recently been limited to clean, well-defined gas phase streams.

Sampling generally is the most difficult problem associated with the on-line analysis of process streams, regardless of the analytical technique. Many gas and liquid process streams are chemically and physically complex and require pretreatment prior to analysis. This has been especially true for mass spectrometry analysis, which generally has utilized a capillary or orifice sample introduction system that is limited to filtered fluids.

Many sampling problems are circumvented by utilizing membrane extraction techniques. In practice, the analysis of organic compounds of interest in liquid and gas streams is most commonly performed off-line after first extracting and concentrating the compounds. In many instances streams containing particulate matter must be filtered prior to analysis. These procedures often are laborious, time-consuming, and require a considerable amount of sample handling. By use of the apparatus and methods according to the invention, however, the on-line extraction and analysis of samples of process liquid and gas streams may be performed continuously, virtually simultaneously, and without the necessity of filtration.

Prior activities in the relevant art have focused on the measurement of compounds contained in the effluent of gas or liquid streams following the treatment thereof in a reactor. The concept of near-simultaneous on-line analysis of both the influent and effluent gas and liquid streams of a reactor, or a plurality of reactors, has not previously been reported. Nevertheless, for complete and accurate characterization of a process, all streams, both influent and effluent, must be analyzed if errors made from assumptions about the content of the influent stream or streams are to be avoided or minimized. The apparatus and method of the invention achieve this objective.

SUMMARY OF THE INVENTION

On-line analyses according to the invention of process streams enable mass balance determinations to be performed for characterization of a process via continuous analysis of the process influent and effluent streams. For a given analyte entering the process, the steady state mass balance equation is:

$$m_{il} + m_{ig} = m_{el} + m_{eg} + m_p$$

where m denotes the mass flow rate for the analyte in the stream designated by the subscript, and the subscripts i, e, l, and g denote the influent, effluent, liquid, and gas streams, respectively. The mass flow rate due to uptake of a compound of interest by the process is designated $m_p$. The values for $m_{il}$, $m_{ig}$, $m_{el}$ and $m_{eg}$ are determined from the on-line analysis of the streams, and $m_p$ is calculated.

On-line characterization of a process stream is accomplished by the extraction of one or more samples of analytes or compounds of interest from the process stream containing multiple compounds and on-line analysis of the extracted samples to enable a determination to be made of the concentration of the analytes as a function of real time. Many process streams may be characterized by a single analyzer in this manner by selectively analyzing the extracted compound from each stream. The extraction step advantageously may be performed by means of a membrane separator to extract from the stream a sample of the particular analyte or analytes of interest.

A process gas or liquid stream under analysis may, for example, have at least a portion thereof pumped through a conduit to a reactor through means, such as a membrane separator, for extracting a sample of a selected analyte of interest from the reactor influent. Following treatment of the stream in the reactor, the effluent process stream may pass through a membrane separator which extracts some or all of the selected analyte remaining in the stream following treatment. By analyzing the analytes extracted from the influent and effluent streams it is possible to characterize them and determine the concentrations of the selected analytes, thereby making possible an evaluation of the effectiveness of the treatment to which the process stream is subjected. Typically, the effluent stream will retain residual analyte(s) since the extraction may not be 100% and, if so, the effluent may be recycled back into the process stream or delivered to a collector, drain, or vent.

Each membrane separator serves to extract the analyte(s) by a selective permeation process involving permeation through the membrane or, alternatively, by rejection of the analyte while selectively permeating the unwanted components of the process stream, thereby inhibiting unwanted components from entering the analyzer. If the unwanted components are solids, typically the first mentioned mode of analyte extraction is chosen.

Samples of analyte(s) from multiple process streams may be extracted and analyzed by the methods and apparatus of the invention. The samples extracted from multiple streams may be conducted through tubes from the extraction means to a stream-select device of known kind. The stream-select device is used to select which of the samples extracted from multiple streams are to be analyzed independently of one another by a common analyzer.

Thus, at any time, one or more analytes extracted from any selected one of a number of streams may be conducted to the common analyzer for determination of the concentration as a function of time. A suitable analyzer may be a mass spectrometer, a gas or liquid chromatograph, an infrared spectrometer, or another analyzer capable of accurately detecting the analyte species and concentration of the analyte. The nonselected streams of extracted analyte(s) may be purged by a gas or liquid stream or evacuated by a vacuum pump in order to prevent accumulation of extracted analyte in the membranes and tubes. For example, the stream-select device may be controlled manually or by a computer or other timing device so that analyte(s) extracted from different process streams may be sampled at predetermined intervals. The membrane separators and the stream-select device preferably are maintained at a constant, selected temperature because, as is well-known, in permeation processes a membrane selective mechanism is generally temperature variable.

The invention is capable of performing real-time analyses with high sensitivity over a wide dynamic range of liquid and/or gas samples of highly complex process streams for mass balance determinations and consequent process control and optimization.

THE DRAWINGS

Apparatus and methods according to presently preferred embodiments of the invention are illustrated in the accompanying drawings, wherein.

THE DISCLOSED EMBODIMENTS

Figure 1:
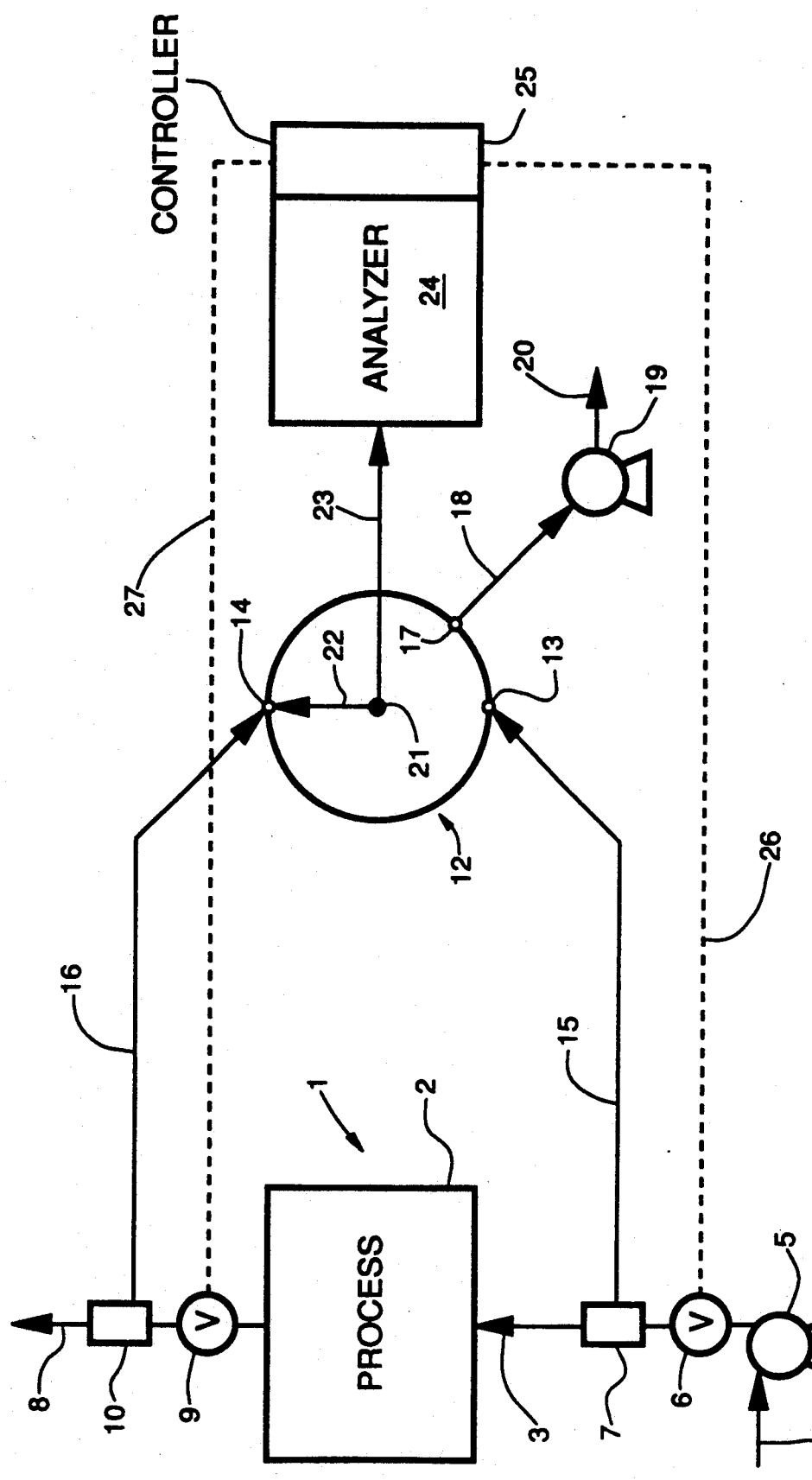
FIG. 1 is a diagrammatic view of apparatus adapted for use in the on-line analysis of a single process stream which flows toward, through, and beyond a stream treatment zone.

The apparatus shown in FIG. 1 is particularly adapted for use in the analysis of continuously flowing streams of gases or liquids, or both, to identify and characterize extractable substances contained in such stream. The apparatus comprises a process or treatment zone 1 formed by suitable means such as a retort or reactor 2, into, through, and beyond which a process stream flows. The stream flows toward the reactor through an influent inlet 3 in communication with a gas or liquid source 4 via a variable speed pump 5 and in communication with the reactor 2 via an adjustable, flow control valve 6 and a membrane separator 7 the construction and operation of which will be described hereinafter.

In the embodiment disclosed in FIG. 1 the gas or liquid may flow into, through, and out of the treatment zone 1 at variable, controlled flow rates as determined by the pump 5 and the valve 6. The reactor 2 may be any one of a number of suitable kinds and is capable of containing a solid reagent, such as activated charcoal, an active or inactive biodegrading mass (biomass), or a liquid or a gas in addition to or to the exclusion of the other reagents referred to above. The contents of the reactor will depend upon the specific process streams to which the apparatus is applied, and such process streams include waste water; fermentation reactions; stripping, distillation, and absorption columns; and degasing units, for example.

An effluent outlet 8 communicates with the reactor 2 via an adjustable valve 9 and a membrane separator 10 similar to the separator 7. The outlet 8 communicates also with a drain, vent, the treatment zone 1, or other destination as may be appropriate.

The apparatus includes a rotary selector switch 12 having a plurality of inlet ports 13 and 14 connected by tubes 15 and 16 to the membrane separators 7 and 10, respectively. The selector switch has an exhaust port 17 connected via a line 18, an exhaust pump 19, and a tube 20 to a collector, vent, or other suitable device. The selector switch may be any suitable stream-select device, such as a rotary switching valve produced by Valco Instruments Co., Inc., or a manifold with multiple 3-way valves of the kind that can be obtained from Skinner Valve Co. A manifold with multiple valve-membrane combinations such as described in co-pending application Ser. No. 455,472, filed Dec. 22, 1989, and now U.S. Pat. No. 5,019,139 also may be used.

The switch 12 has a rotor 21 which carries a coupling tube 22 that may be connected to any selected one of the ports in response to rotation of the rotor. The switch also includes a stationary delivery tube 23 in communication with an analyzer 24. The analyzer is one that is appropriate for analysis of the kinds of analytes extracted from the fluid streams by the separators. For example, the analyzer may be a Balzers QMG 511 quadrupole mass spectrometer.

Operatively coupled to the analyzer 24 in known manner is a controller 25. The controller may be a computer such as that designated PDP 11-73 by Digital Equipment Corporation. The controller is connected to a power source (not shown) and to the valves 6 and 9 by control lines 26 and 27, respectively, for adjusting the valves to vary the rates of flow of fluid therethrough.

The membrane of the separator 7 is permeable to a selected compound of interest contained in the influent fluid and the membrane in the separator 10 is permeable to the same or different compound, depending on the process occurring in the zone 1, whether the process is one which extracts or adds compounds, and the analysis to be made.

In the use of the apparatus thus far described, influent process fluid is delivered to the treatment zone 1 via the pump 5 and the inlet 3, the valve 6, and the membrane separator 7. All of the influent fluid flows through the separator 7. The rate of flow of the influent fluid is controlled by the pump, the valve, or both. The separator 7 extracts a sample of the selected compound from the influent whence it is delivered to the port 13 of the switch 12 via the tube 15. Movement of the rotor 21 of the switch 12 will establish communication between the port 13 and the analyzer 24 to enable the extracted sample to be identified and characterized.

The fluid delivered to the treatment zone 1 is acted upon by whatever reagent or reagents are accommodated in the reactor 2. Such reagent(s) may comprise a living or inert biomass, another liquid, a gas, or a solid such as particles of activated charcoal. The specific reagent utilized will be selected for its ability to react in a known manner with the particular fluid and compounds therein introduced to the treatment zone.

Fluid which traverses the reactor 2 will react with the reagent(s) and be discharged through the effluent outlet 8 via the valve 9 and pass through the separator 10 to a collector, drain, or back to the treatment zone or other destination. The membrane of the separator 10 will extract a sample containing some or all of the same compound remaining (if any) in the effluent fluid and deliver it via the tube 16 to the port 14. Adjustment of the rotor 21 to connect the tube 22 to the port 14 will enable the extracted sample to be delivered to the analyzer 24 for analysis.

Whenever the separators 7 and 10 are not being used for analysis purposes, they, their respective tubes 15 and 16, and the ports 13 and 14 are purged by the pump 19, the line 18, and the port 17, it being understood that internal passages are provided in the switch 12 for this purpose, as is conventional.

By comparing the analyses of the influent and effluent fluids, the presence and concentration of the compound of interest in the effluent may be detected and compared with the concentration of such compound in the influent fluid, thereby enabling the effectiveness of the treatment performed in the treatment zone 1 be evaluated. If it is determined that more or less residence time of the influent fluid in the reactor is required, the valves 6 and 9 or the pump 5 may be adjusted appropriately, either manually or automatically by the controller 25 via the connections 26 and 27, respectively.

It also is possible from the comparison of the analyses of the influent and effluent fluid samples to ascertain the effectiveness of the reagent or reagents that may be accommodated in the reactor, thereby enabling appropriate decisions to be made concerning modification or replacement of such reagents.

It will be apparent from the foregoing that the apparatus disclosed thus far is capable of substantially simultaneous on-line analysis of influent and effluent streams, any delay between successive analyses being that necessitated by adjustment of the rotor 21 of the selector switch 12. It also will be apparent that the treatment to which the influent fluid is subjected in the treatment zone may be controlled or varied by adjustment of the rates of flow of such streams. During a given analysis period, however, the rates of flow of the streams should be maintained constant.

Among the compounds that have been analyzed with apparatus and methods according to the invention are toluene; dichloromethane; benzene; carbon tetrachloride; ethylbenzene; chloroform; styrene; 1, 1, 1-trichloroethane; 1, 1, 2-trichloroethane; chlorobenzene; tetrachloroethane; and bromoform. However, the invention is applicable to any compound to which the membrane of the separator is permeable.

An important advantage of the invention is its ability to analyze fluids on-line without the necessity of filtering such fluids. This advantage is obtainable by the use of fluid lines and tubes having bores of such dimensions as to pass not only the fluids, but also any particles entrained therein. Further, as will be explained in more detail, the bores or passages through the membrane separators are so constructed that they, too, will pass the fluids and entrained contents.

Figure 2:
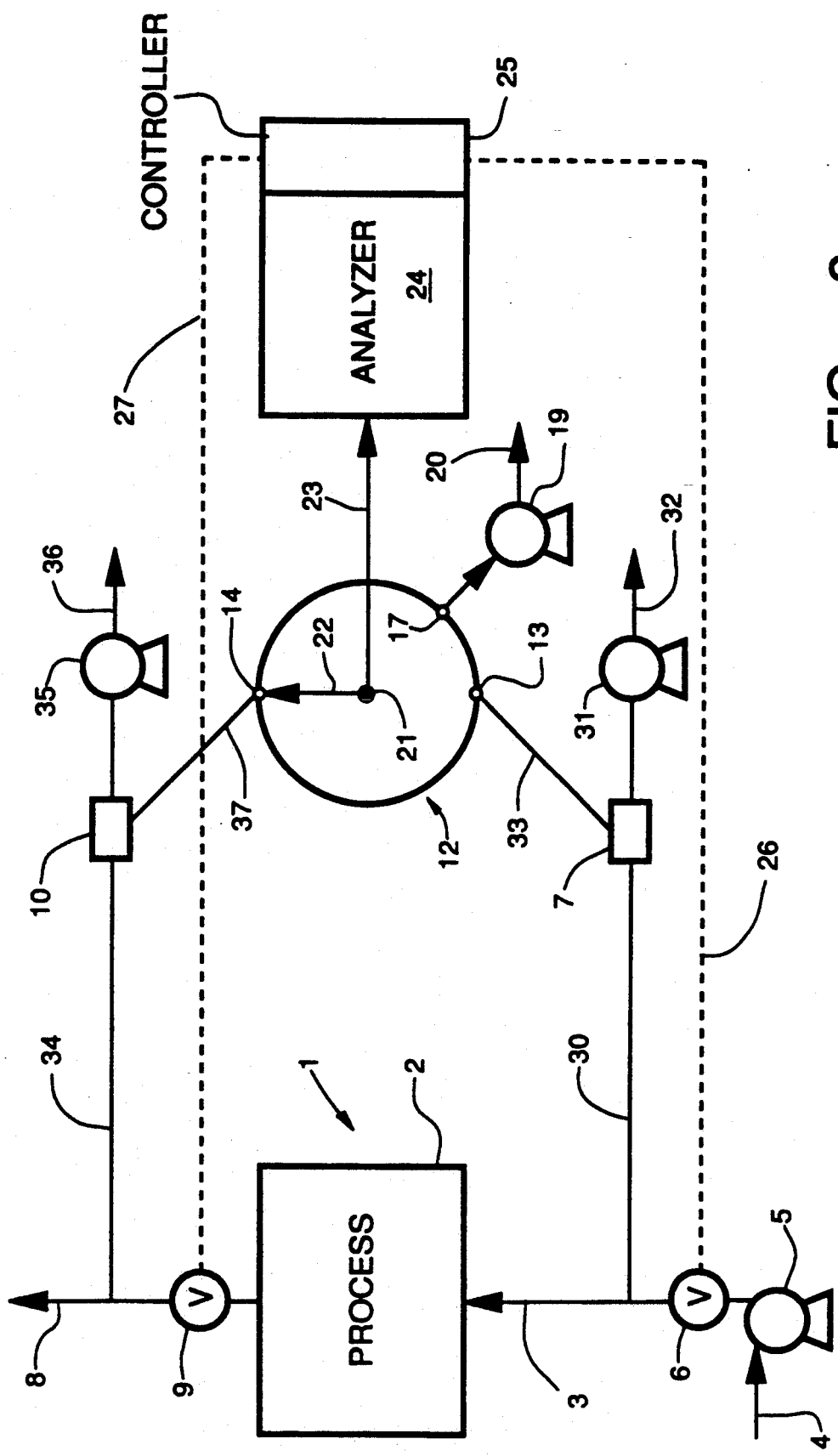
FIG. 2 is a view similar to FIG. 1, but showing apparatus wherein portions of the influent and effluent streams are diverted to membrane separators.

The apparatus disclosed in FIG. 2 corresponds generally to that disclosed in FIG. 1 but differs from the latter by avoiding the necessity of having all of the influent and effluent fluids pass through the separators 7 and 10. In the modified embodiment the membrane separator 7 is positioned in a tube 30 which branches off the influent inlet 3 and extends to a pump 31 and thence to a collector, drain, or back to the source 4 via a line 32. The separator 7 is coupled to the port 13 of the selector switch 12 via a tube 33. A branch tube 34 extends from the effluent outlet 8 through the membrane separator 10 to a pump 35 and from the latter to a collector, drain, or other destination via a line 36. A tube 37 extends from the separator 10 to the port 14 of the switch 12.

The analysis operation of the embodiment shown in FIG. 2 corresponds generally to that described earlier. Preferably, the pumps 31 and 35 are variable speed pumps so as to enable variations in flows of the diverted fluids to be obtained.

Figure 3:
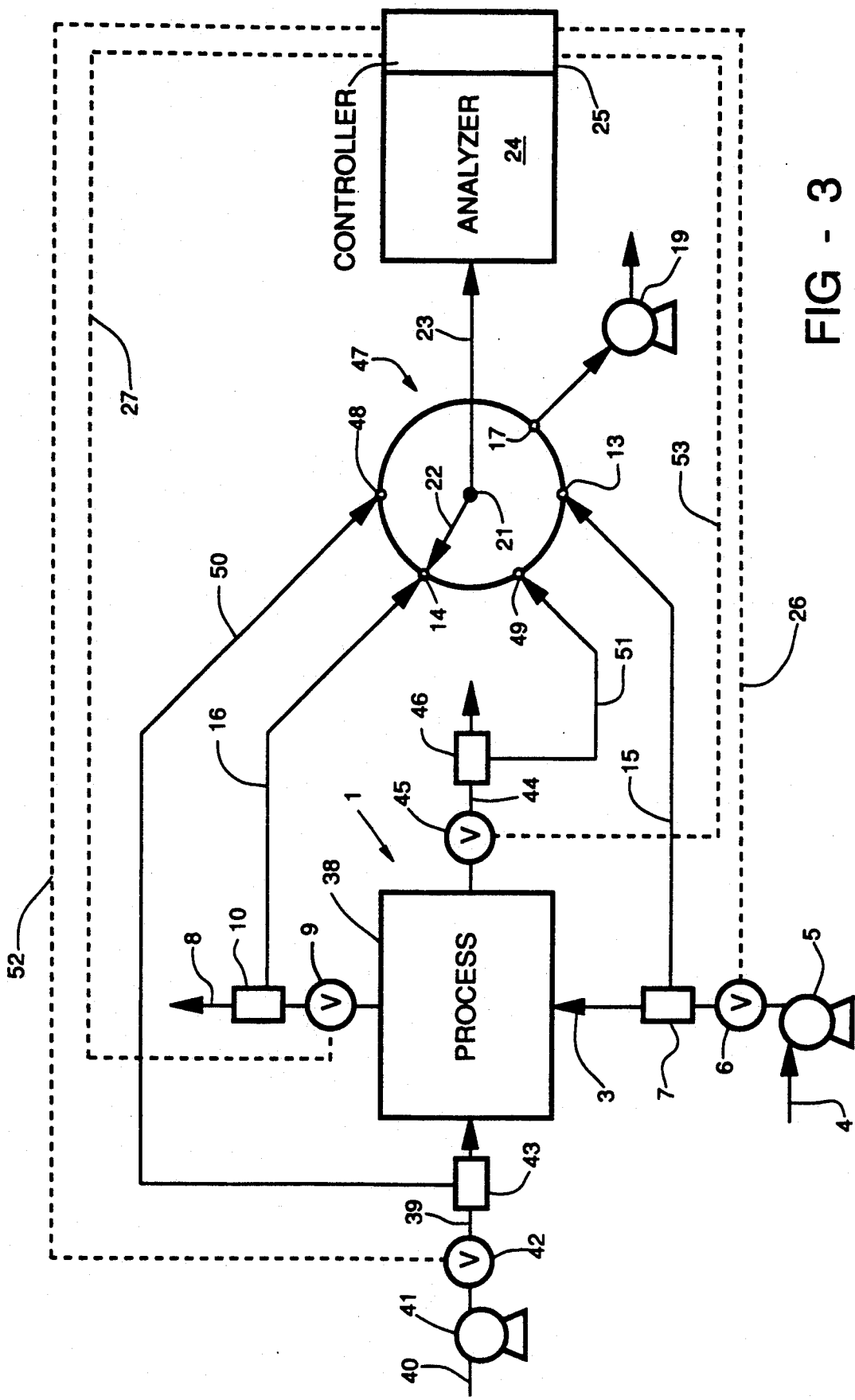
FIG. 3 is a view similar to FIG. 1, but showing apparatus adapted for use with two separate process streams.

In the embodiment shown in FIG. 3 the treatment zone 1 comprises a retort, reactor, or the like 38 to which are fitted the influent inlet 3, the effluent outlet 8, the adjustable valves 6 and 9, the pump 5, and the one fluid source 4 corresponding in all respects to the embodiment shown in FIG. 1. In addition, however, the embodiment of FIG. 3 includes a second influent inlet 39 in communication with a second fluid source 40 via a variable speed pump 41 and an adjustable valve 42, the inlet 39 extending through a membrane separator 43 and communicating with the reactor 38. Also included in the embodiment of FIG. 3 is a second effluent outlet 44 which communicates with the reactor 38 via an adjustable valve 45. The outlet 44 also communicates with a similar membrane separator 46 via a tube 47 and thence with a drain, collector, or other destination.

The embodiment of FIG. 3 includes a selector switch 47 like the switch 12 except that it has two additional ports 48 and 49. The port 48 communicates with the separator 43 via a tube 50 and the port 49 communicates with the separator 46 via a tube 51.

Finally, the embodiment of FIG. 3 differs from the FIG. 1 embodiment by the inclusion of valve control lines 52 and 53 extending between the controller 25 and the valves 42 and 45, respectively.

In the use of the embodiment of FIG. 3 a first influent fluid may be introduced to the treatment zone 1 via the influent inlet 3 and a second influent fluid may be introduced to the treatment zone via the influent inlet 39. The fluids in the treatment zone may be mingled or maintained separate from another depending on the kind of processes that are to be analyzed. A first effluent fluid passes through the outlet 8 as described earlier and a second effluent fluid passes via the outlet 44 through the valve 45 and the separator 46 to a suitable destination.

The separators 7, 10, and 43, 46 extract samples of selected compounds for analysis in the manner hereinbefore explained. The compounds analyzed may be the same or different from one another.

Figure 4:
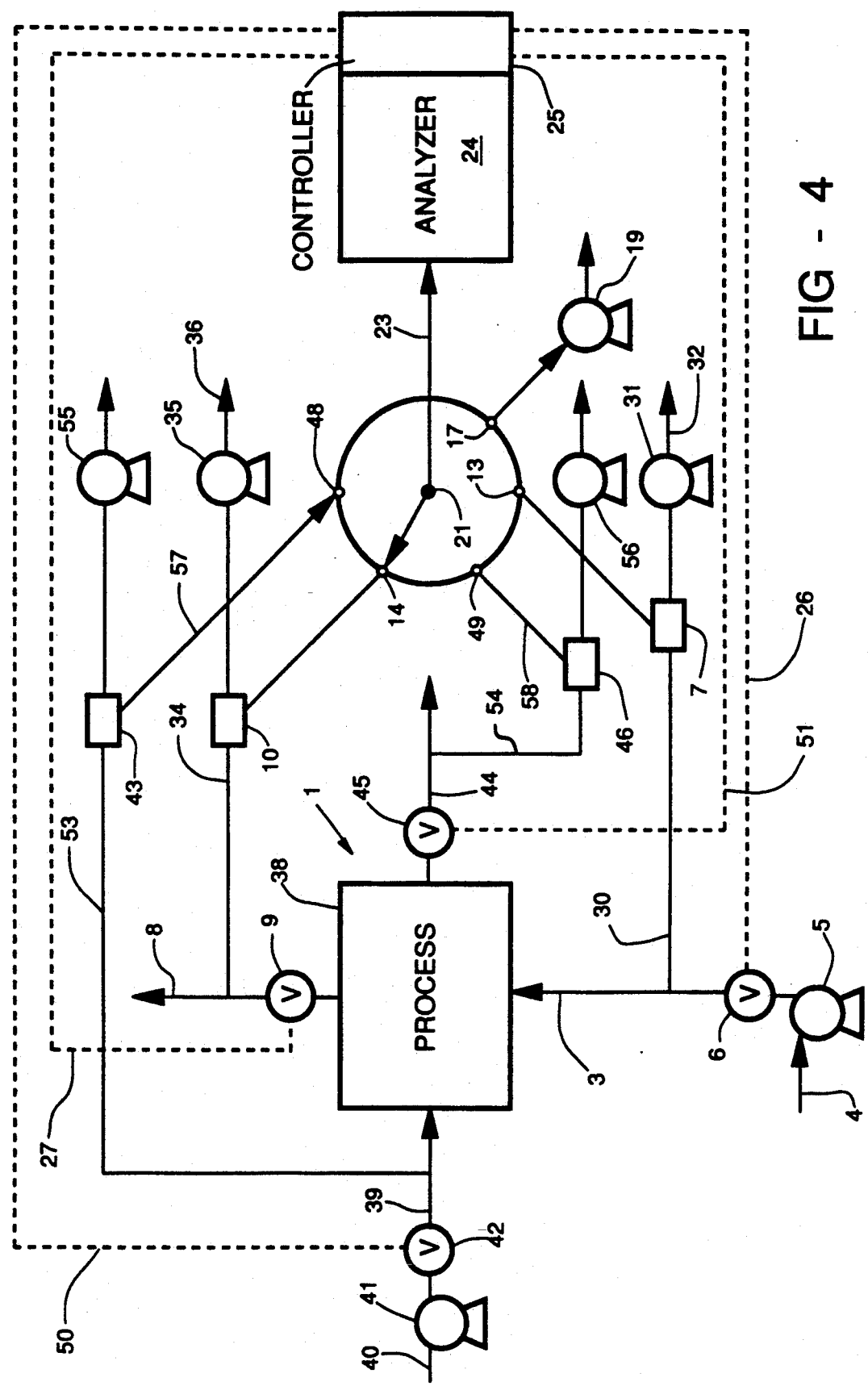
FIG. 4 is a view similar to FIG. 3, but showing portions of the influent and effluent streams diverted to membrane separators.

In the embodiment of FIG. 3 all of the influent and effluent fluids pass through the respective separators. In the embodiment of FIG. 4, however, portions of the influent and effluent fluids to be analyzed are branched off from the respective inlets and outlets so as to avoid having all of the fluids pass through the separators. Thus, in FIG. 4 the separators 43 and 46 are installed in branch lines 53 and 54 which extend from the influent inlet 39 and the effluent outlet 44, respectively, to drains, collectors, or the like via variable speed pumps 55 and 56. The separator 43 communicates with the port 48 via a tube 57 and the separator 46 communicates with the port 49 via a tube 58.

The embodiment shown in FIG. 4 may be operated in the same manner as that disclosed in FIG. 3.

Figure 5:
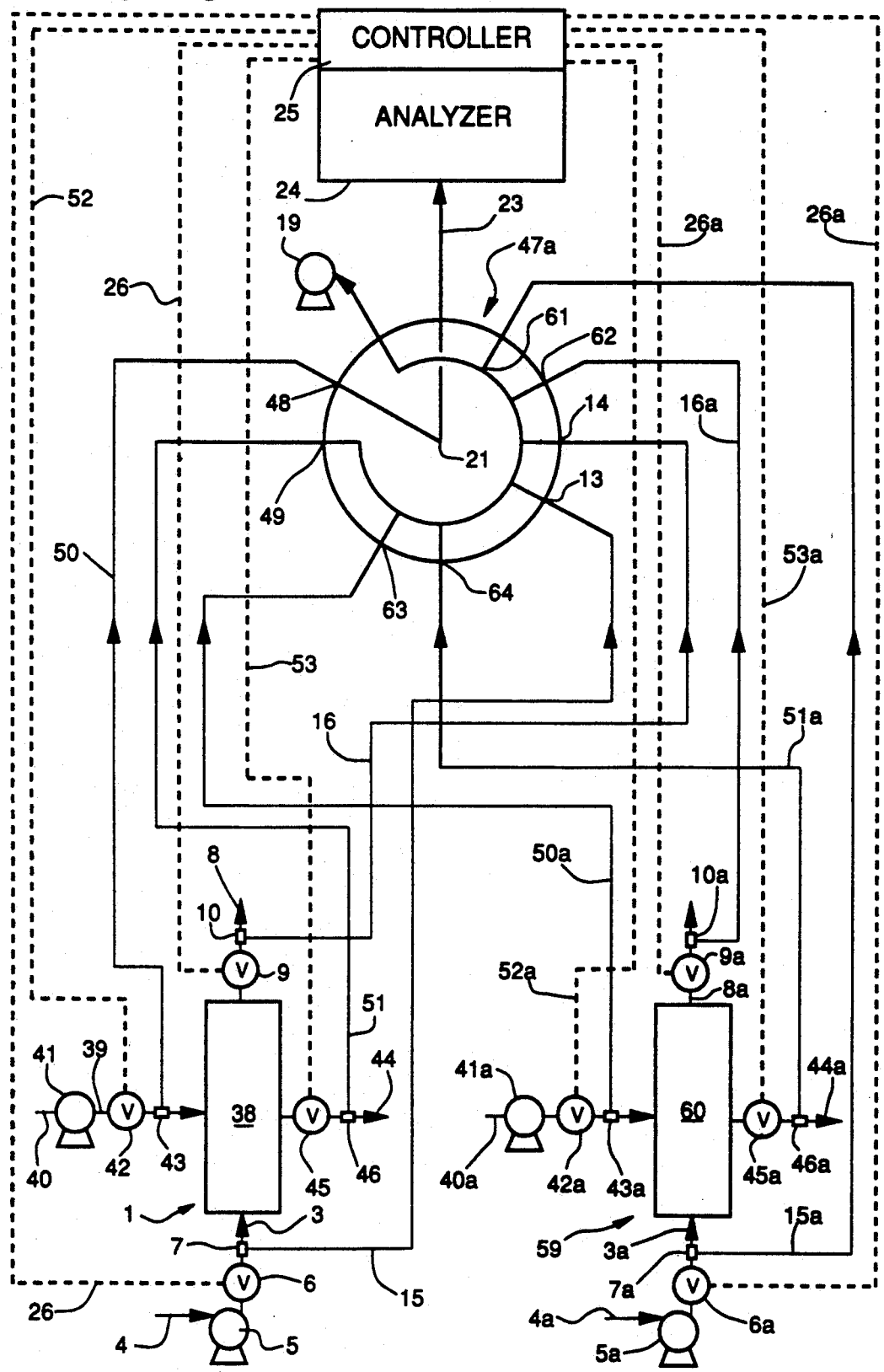
FIG. 5 is a diagrammatic view illustrating apparatus having multiple treatment zones adapted for the analysis of multiple streams.

FIG. 5 discloses apparatus generally similar to that shown in FIG. 3 with the exception that the FIG. 5 embodiment includes a second treatment zone 59 having a reactor or retort 60 like the corresponding unit 38 shown in FIG. 3. The unit 60 is provided with influent fluid inlets and outlets like those shown in FIG. 3. Accordingly, the same reference characters are used for the second treatment zone and associated parts, followed by the suffix a.

The embodiment of FIG. 5 also differs from that of FIG. 3 in that the selector switch 47a includes four additional ports 61, 62, 63, and 64 connected to the respective tubes 15a, 16a, 50a, and 51a.

The operation of the apparatus to analyze the fluids flowing through each of the treatment zones 1 and 59 shown in FIG. 5 corresponds to that described earlier with reference to the analysis of the fluids flowing through the treatment zone 1 of FIG. 3. Again, the compounds extracted from the several streams associated with the reactors 38 and 60 may be the same or different from one another.

Figure 6:
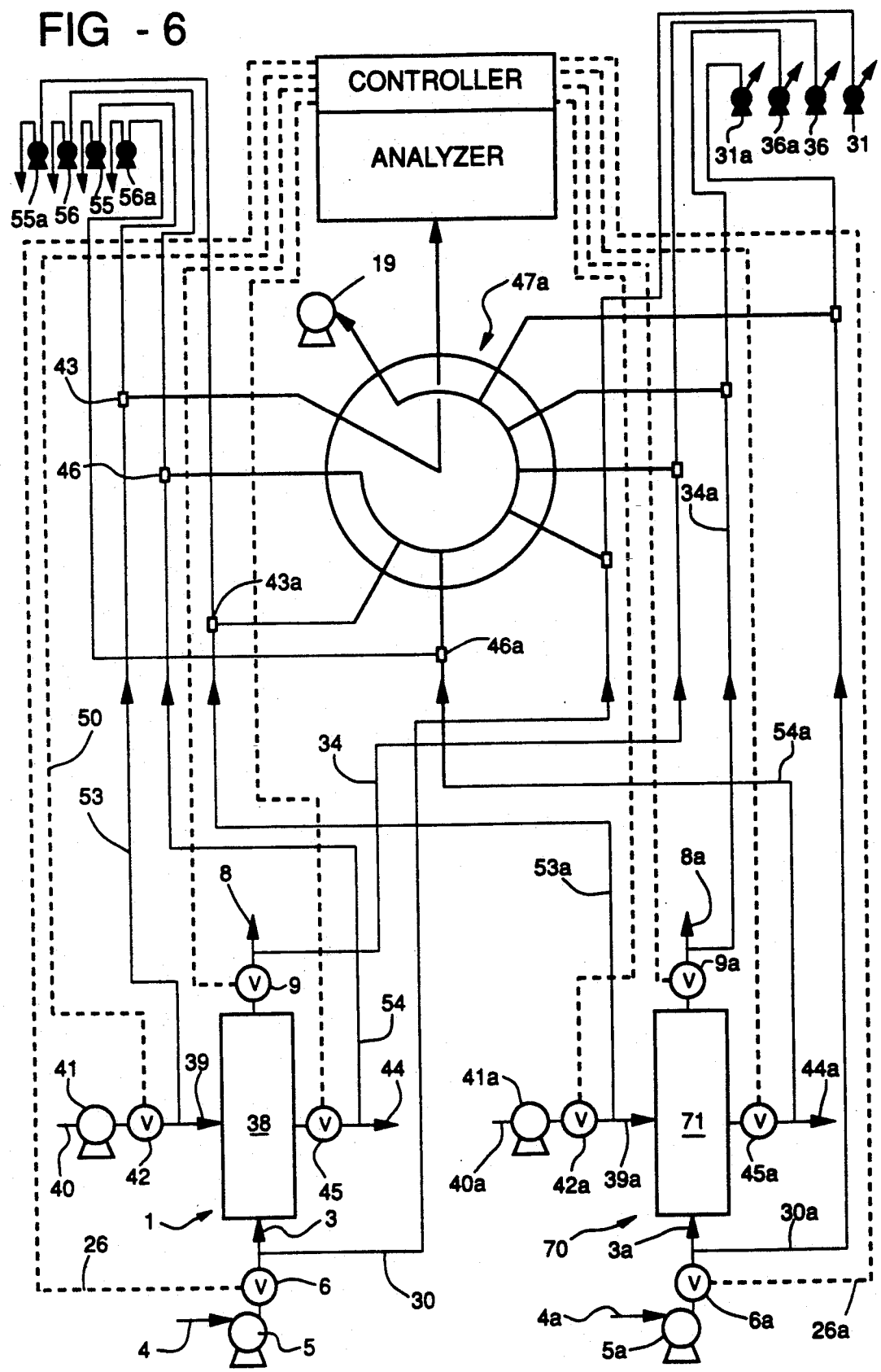
FIG. 6 is a view similar to FIG. 5 but showing diversion of the multiple streams to the separators.

The embodiment shown in FIG. 6 corresponds substantially to that shown in FIG. 4 and differs structurally from the latter largely in that the embodiment shown in FIG. 6 includes a second treatment zone 70 comprising a retort or reactor 71 like the corresponding reactor 60 of FIG. 5. Again, parts associated with the second treatment zone 70 corresponding to the treatment zone 1 of FIG. 4 are identified by corresponding reference characters followed by the suffix a. The embodiment of FIG. 6 makes use of a switch 47a like that shown in FIG. 5.

The analyses operations of each of the treatment zones 1 and 70 of FIG. 6 embodiment correspond to those associated with the apparatus shown in FIG. 5.

In those instances in which the composition of the influent stream or streams is known and remains constant, it is not necessary to analyze such streams repetitively inasmuch as the analyses of the effluent streams will be sufficient to enable the efficiency of the treatment of the process stream or streams to be determined. Thus, it is possible to analyze multiple liquid or gas effluent streams only, such as those exiting the treatment zones shown in FIGS. 3-6, and still evaluate the efficiency of the processes.

Figure 7:
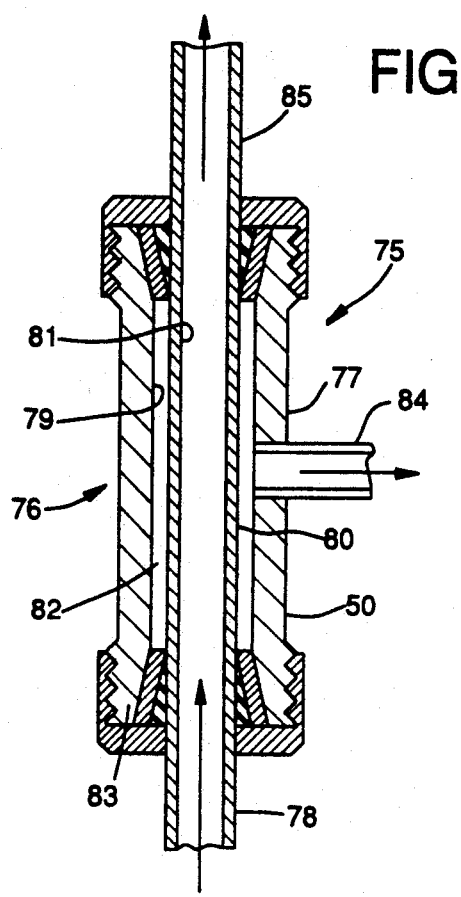
FIG. 7 is a greatly enlarged, cross sectional view of one form of membrane separator suitable for use with the invention.

One membrane separator 75 suitable for use in any of the disclosed embodiments is illustrated in FIG. 7 and comprises a T-shaped body 76 having a tubular section 77 connected to a conduit 78 corresponding to any of the fluid conduits disclosed earlier. The section 77 has a bore 79 in which is accommodated a hollow fiber membrane 80 formed of medical grade tubing manufactured by Dow Corning Corporation. The fiber has a bore 81 in communication with the bore of the conduit 78, but the outside diameter of the fiber 80 is less than the diameter of the bore 79, thereby providing an annular chamber 82 between the fiber and the bore of the section 77. The chamber 82 communicates with a tube 84 that extends to one of the ports of the rotary selector switch referred to earlier. At opposite ends of the section 77 are appropriate seals 83 for providing a fluid tight joint between the separator and the conduits 78 and 85 leading thereto and therefrom.

The bore of the fiber membrane 80 of the separator is of sufficient diameter that whatever substances can pass through the conduit also will pass through the fiber membrane of the separator. Accordingly, filtering of the fluid to be analyzed is not required.

Figure 8:
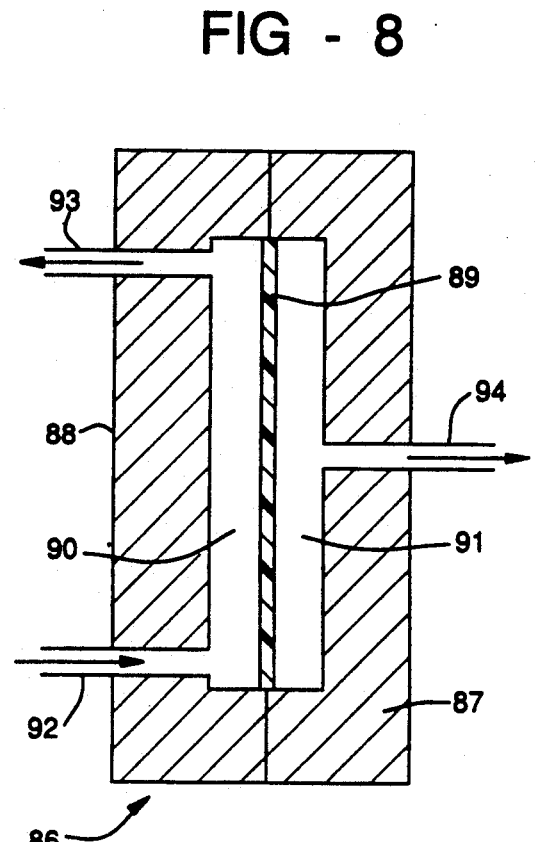
FIG. 8 is an enlarged, diagrammatic cross sectional view of another form of suitable membrane separator.

Other kinds of membrane separators may be utilized with the same advantageous results. FIG. 8 illustrates a sheet type membrane separator 86 comprising a known cell having two body portions 87 and 88 between which a membrane 89 is clamped and sealed to form two chambers 90 and 91. A fluid inlet 92 communicates with the chamber 90 on one side of the membrane, and a fluid outlet 93 communicates with the chamber 90 on the same side of the membrane. The membrane is permeable to one or more compounds which may pass through the membrane and be received in a tube 94 in communication with one of the ports of a rotary selector switch a referred to earlier. The sizes of the bores of the inlet 92 and the outlet 93 and the interior dimension of the chamber 90 are such as to pass whatever is entrained in the fluid, thereby dispensing with any necessity of filtering the fluid.

Figure 9:
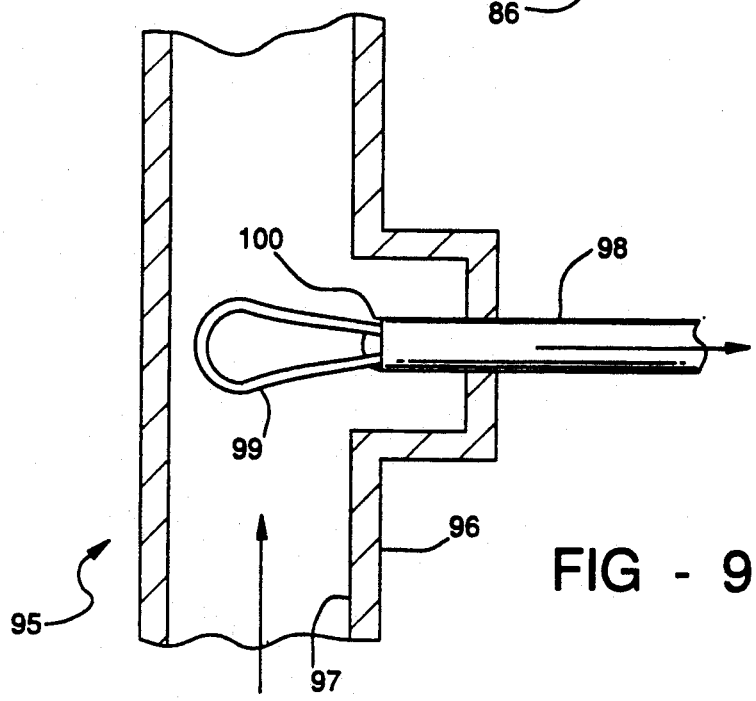
FIG. 9 is an enlarged, fragmentary, diagrammatic cross sectional view of another form of suitable membrane separator.

Another form of suitable membrane separator 95 is shown in FIG. 9 and comprises a fluid conduit 96 having a bore 97 in communication with one end of a tube 98 which leads to one of the rotary selector switches. A hollow, membrane loop 99 has its opposite ends accommodated in a seal 100 fitted into the tube 98 and retained therein by a suitable clamp. The material from which the membrane loop 99 is formed is permeable to the compounds of interest and may be positioned within the conduit 96 in the path of fluid flowing therethrough so as to extract compounds of interest. Again, no filtration is required when a loop membrane of the kind disclosed is used.

In those instances in which the membrane of the membrane separator has pores, the membrane should be so selected that the pores will neither pass nor become plugged by particulate matter in the fluid stream.

The temperature of each of the treatment zones 1 and the separators preferably is maintained substantially uniform and constant in ways that are well known in the art.

The apparatus disclosed herein may be fixed in place, or it may be assembled on a mobile support such as a truck or van for transport and use at a selected site.

The apparatus and methods disclosed herein are similar in some respects to the disclosure of commonly owned application Ser. No. 07/680,663 filed Apr. 4, 1991.

We claim:

1. Apparatus for on-line analysis of at least one fluid stream composed of one or more compounds and flowing at a selected rate to, through, and from a treatment zone, said apparatus comprising means upstream from said zone for extracting a selected substance of interest from influent fluid enroute to said zone; means downstream from said zone for extracting a selected substance of interest from effluent fluid exiting said zone; means for analyzing the extracted substances; and means for delivering the extracted substances independently of one another to said analyzing means.

2. Apparatus according to claim 1 wherein the extracted substances are the same.

3. Apparatus according to claim 1 wherein the substance extracted from the influent fluid is different from the substance extracted from the effluent fluid.

4. Apparatus according to claim 1 including adjustable control means for controlling the rate of flow of said at least one fluid stream.

5. Apparatus according to claim 4 wherein said adjustable control means comprises adjustable valve means.

6. Apparatus according to claim 4 wherein said adjustable control means comprises adjustable fluid pump means.

7. Apparatus according to claim 4 wherein said adjustable control means comprises adjustable valve means, and means for adjusting said valve means.

8. Apparatus according to claim 1 wherein the means for analyzing said substances includes means for determining the concentration thereof.

9. Apparatus according to claim 8 including adjustable control means for controlling the rate of flow of said fluid stream, and means responsive to changes in the concentrations of said substances to actuate said adjustable control means 10. Apparatus according to claim 1 wherein the means for extracting the substance of interest comprises membrane separator means having a membrane permeable to such substance.

11. Apparatus according to claim 10 wherein said membrane separator comprises a body having a chamber therein and a tubular membrane accommodated in said body, said membrane having a bore through which said stream flows.

12. Apparatus according to claim 11 wherein said bore is of such dimension as to accommodate and pass particulate matter entrained in said stream and delivered to said separator means.

13. Apparatus according to claim 10 wherein said membrane separator comprises a body having a sheet membrane therein dividing said body into two chambers through one of which said stream may flow, said one of said chambers being of such dimension as to accommodate particulate material entrained in said stream.

14. Apparatus according to claim 10 wherein said membrane separator comprises a tubular membrane in the form of a loop and accommodated in the flow path of said stream.

15. Apparatus according to claim 1 wherein said fluid stream is gas.

16. Apparatus according to claim 1 wherein said fluid stream is liquid.

17. Apparatus for on-line analysis of multiple fluid streams each of which flows at a selected rate and contains multiple substances, said apparatus comprising means forming a treatment zone; means for conducting each of said streams along a path to, through, and beyond said zone; first and second extracting means upstream and downstream respectively from said zone for extracting a selected substance of interest from one of said streams prior to and following passage of said one of said streams through said zone; third and fourth extracting means upstream and downstream respectively from said zone for extracting a selected substance of interest from another of said streams prior to and following passage from another of said streams through said zone; means for analyzing each of the extracted substances; and means for delivering each of the extracted substances independently of one another to said analyzing means.

18. Apparatus according to claim 17 wherein the substance extracted by said first and second extracting means is the same and the substance extracted by said second and third extracting means is the same.

19. Apparatus according to claim 18 wherein the substance extracted by said first and second extracting means is different from the substance extracted by said second and third extracting means.

20. Apparatus according to claim 17 including adjustable control means for controlling the rate of flow of each of said streams.

21. Apparatus according to claim 20 wherein said adjustable control means comprises adjustable valve means.

22. Apparatus according to claim 20 wherein said adjustable control means comprises adjustable fluid pump means.

23. Apparatus according to claim 20 wherein said adjustable control means comprises adjustable valve means, and means for adjusting said valve means.

24. Apparatus according to claim 17 wherein the means for analyzing each of the extracted substances includes means for determining the concentration thereof.

25. Apparatus according to claim 24 including adjustable control means for controlling the rate of flow of said fluid, and means responsive to changes in the concentrations of said substances for actuating said adjustable control means.

26. Apparatus according to claim 17 wherein the means for extracting at least one of the substances of interest comprises membrane separator means having a membrane permeable to said one or the substances.

27. Apparatus according to claim 17 wherein the means for extracting each of the substances of interest comprises membrane separator means having a membrane permeable to such substance.

28. Apparatus according to claim 17 wherein said membrane separator comprises a body having a chamber therein and a tubular membrane accommodated in said chamber, said membrane having a bore through which said stream flows.

29. Apparatus according to claim 28 wherein said bore is of such dimension as to accommodate particulate matter entrained in said stream.

30. Apparatus according to claim 17 wherein said membrane separator comprises a body having a sheet membrane therein dividing said body into two chambers through one of which said stream may flow, said one of said chambers being of such dimension as to accommodate particulate material entrained in said stream.

31. Apparatus according to claim 17 wherein said membrane separator comprises a tubular membrane in the form of a loop and accommodated in said chamber.

32. Apparatus according to claim 17 wherein all of said fluid streams are gases.

33. Apparatus according to claim 17 wherein at least one of said fluid streams is gas and at least another of said fluid streams is liquid.

34. Apparatus according to claim 17 wherein all of said fluid streams are liquids.

35. A method of analyzing on-line at least one fluid stream containing a plurality of substances and flowing at a selected rate to, through, and beyond a treatment zone in which said fluid is subjected to treatment, said method comprising extracting from said stream upstream from said zone a first sample containing a substance of interest; extracting from said stream downstream from said zone a second sample containing a substance of interest; and analyzing the respective extracted samples to determine the concentrations of the substances therein.

36. The method according to claim 35 including adjusting the rate of flow of said stream through said zone.

37. The method according to claim 35 including extracting said first sample directly from the stream.

38. The method according to claim 35 including extracting said second sample directly from the stream.

39. The method according to claim 35 including diverting from said zone a portion of the fluid flowing toward said zone and extracting said first sample from the diverted portion of said fluid.

40. The method according to claim 39 including diverting a portion of the fluid flowing from said zone and extracting said second sample from such diverted portion of said fluid.

41. The method according to claim 35 including diverting a portion of the fluid flowing from said zone and extracting said second sample from such diverted portion of said fluid.

42. The method according to claim 35 including delivering the extracted samples independently of one another to a common analyzer in which the analyzing is performed on each of said samples independently of one another.

43. The method according to claim 42 wherein each of said samples is extracted by a membrane separator having a membrane permeable to said substance of interest.

44. The method according to claim 35 wherein said fluid stream is gas.

45. The method according to claim 35 wherein said fluid stream is liquid.

46. A method of analyzing on-line a plurality of fluid streams each containing substances of interest and flowing at a selected rate to, through, and beyond a treatment zone at which each such stream is subjected to treatment, said method comprising extracting from one of said streams upstream from its treatment zone a first sample of a substance of interest; extracting from said one of said streams downstream from its treatment zone a second sample of the same substance; extracting from another of said streams upstream from its treatment zone a first sample of a substance of interest; extracting from said another of said streams downstream from its treatment zone a second sample of the same substance; analyzing each of the first and second samples extracted from said one of said streams to determine the concentration of the substance of interest present in each of said samples; and analyzing each of the first and second samples extracted from said another of said streams to determine the relative concentration of the substance of interest in each of said samples.

47. The method according to claim 46 wherein the analyzing of each of said samples is performed in a common analyzer and wherein each of said samples is delivered to and analyzed in said analyzer independently of the other samples.

48. The method according to claim 46 including adjusting the rate of flow of each of said streams to vary the residence time of each of said streams in its treatment zone.

49. The method according to claim 46 including extracting each of said samples with a membrane separator having a membrane permeable to the substance of interest.

50. The method according to claim 46 wherein each of said first samples is extracted directly from the stream flowing toward the associated treatment zone.

51. The method according to claim 46 wherein each of said second samples is extracted directly from the stream flowing beyond the associated treatment zone.

52. The method according to claim 46 including diverting a portion of each of the streams flowing toward the associated treatment zone and extracting the first sample from the associated diverted portion.

53. The method according to claim 46 including diverting a portion of each of the streams flowing beyond the associated treatment zone and extracting the second sample from the associated diverted portion.

54. The method according to claim 46 wherein all of said fluid streams are gas.

55. The method according to claim 46 wherein at least one of said streams is gas and at least another of said streams is liquid.

56. The method according to claim 46 wherein all of said streams are liquid.

57. Apparatus for on-line analysis of multiple effluent fluid streams containing at least one extractable substance of interest and exiting a treatment zone following treatment in said zone of at least one influent fluid stream of known composition, said apparatus comprising a number of extraction means corresponding to the number of said effluent streams, each of said extraction means being operable to extract from a respective one of said effluent streams a selected substance of interest; analyzing means for characterizing said selected substance; and means for delivering independently of one another the selected substance extracted by each of said extraction means to said analyzing means.

58. A method of analyzing on-line multiple effluent fluid streams containing at least one extractable substance of interest and exiting a treatment zone following treatment in said zone of at least one influent fluid stream of known composition, said method comprising extracting from each of said effluent streams an extractable substance of interest; delivering each extracted substance independently to analyzing means; and independently analyzing each extracted substance.

* * * * *